United States Patent [19]
Vlacancich

[11] Patent Number: 5,529,494
[45] Date of Patent: Jun. 25, 1996

[54] DENTAL TOOL DRIVING DEVICE

[76] Inventor: Tanya Vlacancich, 14-36 132nd St., College Point, N.Y. 11356

[21] Appl. No.: 374,082

[22] Filed: Jan. 18, 1995

[51] Int. Cl.⁶ ..................................................... A61C 1/02
[52] U.S. Cl. .......................................... 433/105; 433/118
[58] Field of Search .................................... 433/105, 118, 433/112, 122, 123

[56] References Cited

U.S. PATENT DOCUMENTS

| | | | |
|---|---|---|---|
| 169,347 | 11/1875 | Evans | 433/112 |
| D. 244,938 | 7/1977 | Viazzoli | D24/8 |
| 462,530 | 11/1891 | Booth | 433/118 |
| 1,329,837 | 2/1920 | Hook | 433/141 |
| 1,378,433 | 5/1921 | Vogelzang | 433/112 |
| 2,858,703 | 11/1958 | Willcox | 433/118 |
| 2,970,483 | 2/1961 | Schrum | 74/22 R |
| 3,661,018 | 5/1972 | Keefer et al. | 15/22 R |
| 4,299,572 | 11/1981 | McKinney | 433/144 |
| 4,397,055 | 8/1983 | Cuchiara | 15/22 R |
| 4,432,729 | 2/1984 | Pattaleh | 433/118 |
| 4,880,382 | 11/1989 | Moret et al. | 433/118 |
| 4,885,965 | 12/1989 | Weissman | 83/100 |
| 4,954,082 | 9/1990 | Weissman | 433/80 |
| 5,084,978 | 2/1992 | McReynolds | 30/517 |
| 5,145,369 | 9/1992 | Lustig et al. | 433/118 |
| 5,267,579 | 12/1993 | Bushberger | 132/322 |

Primary Examiner—John J. Wilson
Attorney, Agent, or Firm—Michael I. Kroll

[57] ABSTRACT

A dental tool driving device comprising a facility within a housing for driving a driven mechanism. A component within the housing is for selectively placing the driven mechanism in a rotating mode and in an oscillating mode. An element is for coupling a rotatable tool implement to the housing in a removable manner. When the selectively placing component is put in the rotating mode, the driving facility will operate the driven mechanism and cause the rotatable tool implement to turn about an axis. Another element is for coupling the oscillating tool implement to the housing in a removable manner. When the selectively placing component is put in the oscillating mode, the driving facility will operate the driven mechanism and cause the oscillating tool implement to swing back and forth.

9 Claims, 2 Drawing Sheets

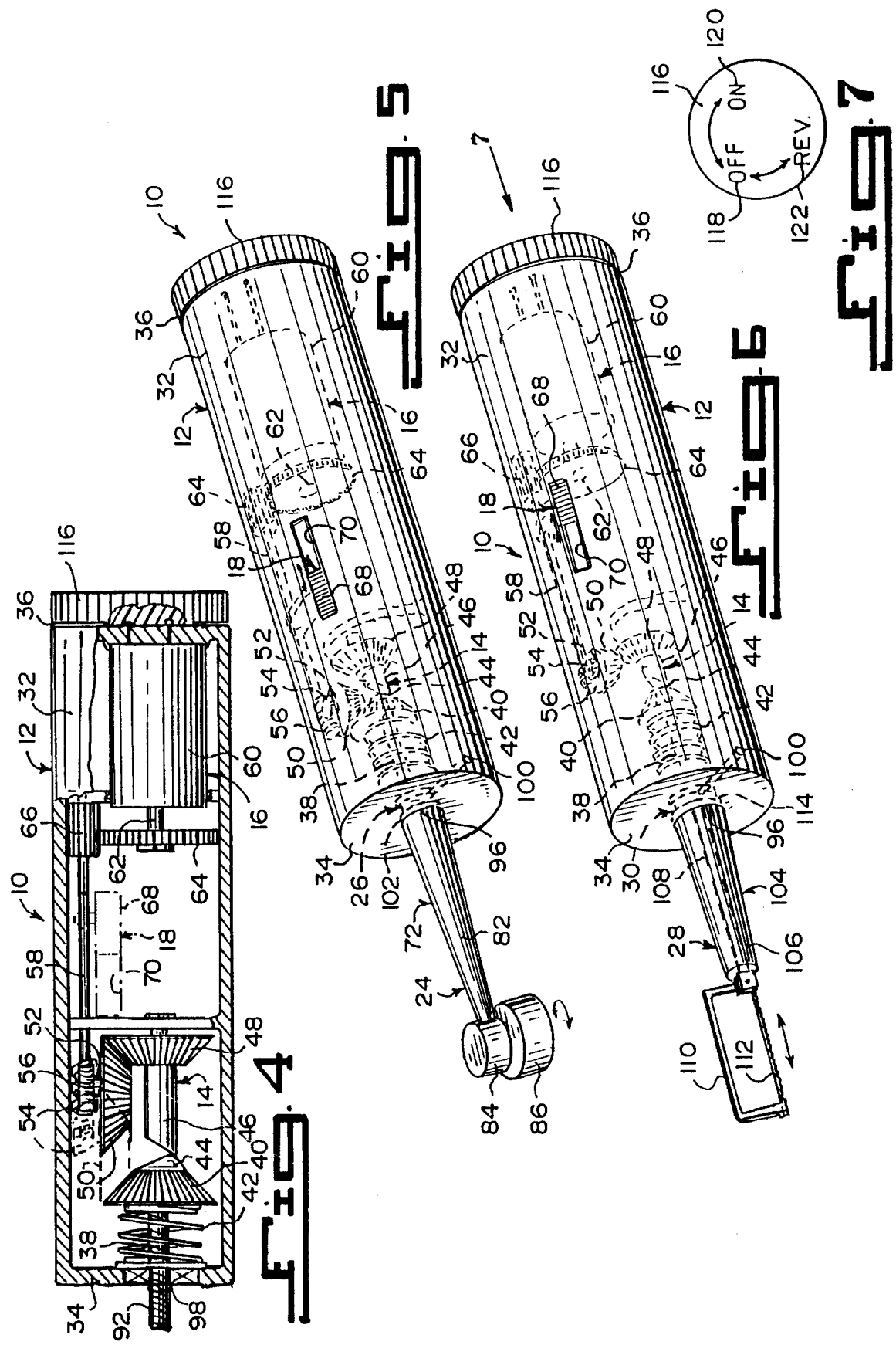

DENTAL TOOL DRIVING DEVICE

BACKGROUND OF THE INVENTION

Field of the Invention

The instant invention relates generally to dental equipment and more specifically it relates to a dental tool driving device.

Description of the Prior Art

Numerous dental equipment have been provided in prior art. For example, U.S. Pat. Nos. 169,347 to Evans; 1,329,837 to Hook; 4,299,572 to McKinney; 4,432,729 to Fattaleh; 4,885,965 to Weissman; 5,084,978 to McReynolds; 5,145,369 to Lustig et al., 5,267,579 to Bushberger and Es. 244,938 to Viazzoli all are illustrative of such prior art. While these units may be suitable for the particular purpose to which they address, they would not be as suitable for the purposes of the present invention as heretofore described.

EVANS, WILLIAM WARRINGTON

IMPROVEMENT IN DENTAL ENGINES

U.S. Pat. No. 169,347

A dental engine, consisting of the combination of casing, a supply pipe, a wheel mounted thereon, an annular waste pipe and a dental tool driven by a flexible shaft connected directly with the water wheel shaft. The parts are adapted to be mounted directly upon an operator's table or other suitable support.

HOOK, JACOB

DENTAL FLOSS TAPE LIP PROTECTOR

U.S. Pat. No. 1,329,837

A device comprising a handle adapted to be supported by a patient. A body is to be braced against the surface of the teeth and a pair of spaced guide openings through which a dental floss is passed and held from contact with the lips.

MC KINNEY, DAVID D.

DENTAL SAW BLADE

U.S. Pat. No. 4,299,572

A saw blade is disclosed for sawing a working model of a dental arch used in fixed crown and bridge work. The blade includes a first number of linear aligned saw teeth and a second number of laterally offset saw teeth, which may be pulled or pushed into a cut initiated in the dental stone by the straight teeth for faster and straighter sawing.

FATTALEH, JOHN B.

PERSONAL HEATH CARE DEVICE

U.S. Pat. No. 4,432,729

A hand-held personal health care device for the polishing of teeth, wherein the appliance containing the cleaning agent is driven in an oscillatory manner.

WEISSMAN, BERNARD

ROTARY SAW FOR SECTIONING DENTAL MODELS

U.S. Pat. No. 4,885,965

A rotary table saw for sectioning dental models having a housing with a base portion and a working table mounted on the base portion. The working table is controllably depressible, so as to be moved upward and downward with respect to the base portion. A motor housed in the base portion drives a rotary blade oriented in a vertical direction. A slit in the work table permits the blade to emerge therethrough as the work table is depressed. A vacuum outlet is placed in flow communication with the surface of the work table during depression of the work table, to remove saw dust from the work table. The dental model is placed on the work table with the blade hidden beneath the work table. The work table is depressed to permit emerging of the rotary blade cutting from the underside of the dental model.

MC REYNOLDS, WILLIAM D.

DENTAL SAW AND ABRASIVE TOOL

U.S. Pat. No. 5,084,978

A dental tool with detachable saw blades and adhesively affixed abrasive strips on the distal ends of a U-shaped handle is for removing the solified resin in posterior and anterior teeth during the placement of porcelain and composite inlays, while keeping the tongue and cheek away from the cutting surfaces. The primary function of the tool is provided by a finger rest to direct the tool force in a gingival direction with stability and control, improving the function and safety of the tool.

LUSTIG, L. PAUL

TYBINKOWSKI, ANDREW

DENTAL TOOL DRIVING APPARATUS HAVING ROTATING AND ROTO-RECIPROCATING MOTIONS

U.S. Pat. No. 5,145,369

A manually deployable power tool for dental treatment and other uses drives an output shaft with continuous rotary motion, combined with selected axial reciprocation of adjustable stroke length. The drive mechanism for imparting this combined motion to the output shaft has a single rotary input drive coupled with an adjustable cam mechanism. The cam mechanism produces the reciprocating motion in response to the driven rotation of the output shaft. The tool drive mechanism has a high degree of axial symmetry, and is arranged to facilitate the delivery of liquid material to the output, tool-carrying end of the output shaft.

BUSHBERGER, TODD E.

OSCILLATING FLOSSING IMPLEMENT

U.S. Pat. No. 5,267,579

A flossing implement includes a hollow handle. A pair of fingers extend from the handle to support therebetween a strand of dental floss. An electric motor in the handle carries an eccentric weight for vibrating the handle. Through the handle, a strand of dental floss is supported at the end of the handle.

VIAZZOLI, ALFRED A.

DENTAL SAW

U.S. Pat. No. Des. 244,938

The ornamental design for a dental saw, substantially as shown.

FIG. 4 is a front end view thereof; and

FIG. 5 is a rear end view thereof.

SUMMARY OF THE INVENTION

Figure 1:
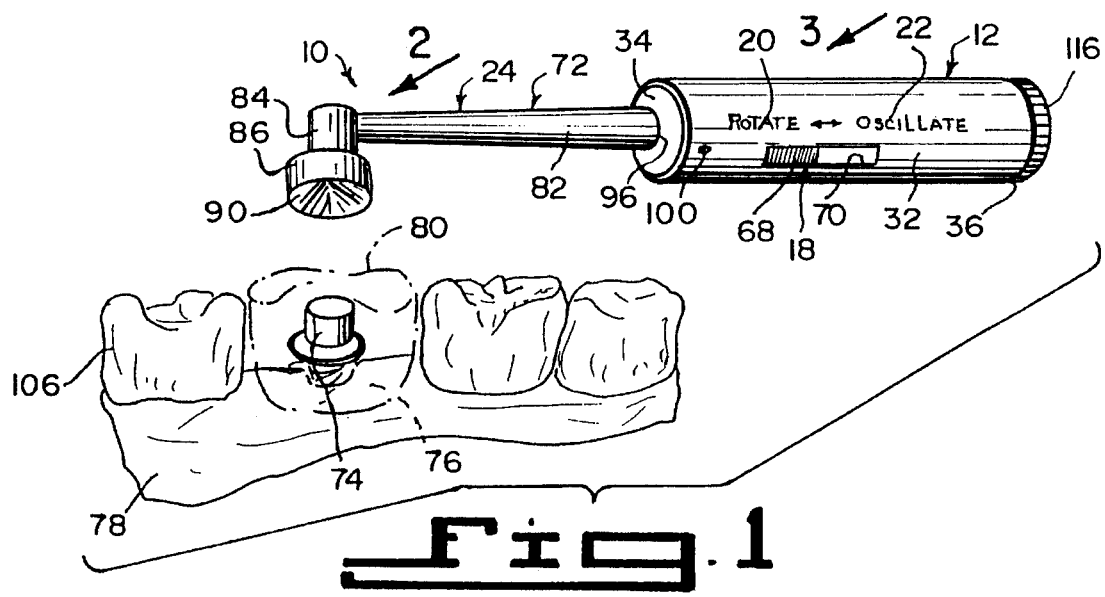
FIG. 1 is a perspective view of a dental saw showing the new design.

A primary object of the present invention is to provide a dental tool driving device that will overcome the shortcomings of the prior art devices.

Another object is to provide a dental tool driving device that can be selectively placed into a rotating mode, so that a tool implement being a head driver assembly can be utilized in inserting a pin implant into the bone below the gum in the mouth.

An additional object is to provide a dental tool driving device that can be selectively placed into a oscillating mode, so that another tool implement being a saw assembly, can be utilized in cutting into a tooth in the mouth or in dental models.

A further object is to provide a dental tool driving device that is simple and easy to use.

A still further object is to provide a dental tool driving device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 1 is a perspective view of the instant invention in the rotating mode that is ready to insert a pin implant into the bone below the gum in the mouth.

Figure 2:
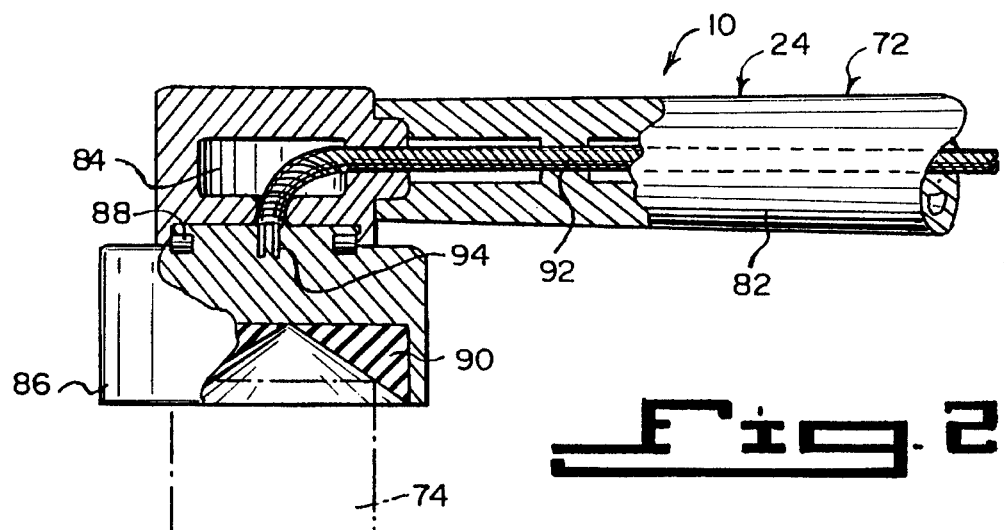
FIG. 2 is a side elevational view showing the side opposite that shown in FIG. 1.

FIG. 2 is an enlarged side view taken in the direction of arrow 2 in FIG. 1, with parts broken away and in section.

Figure 3:
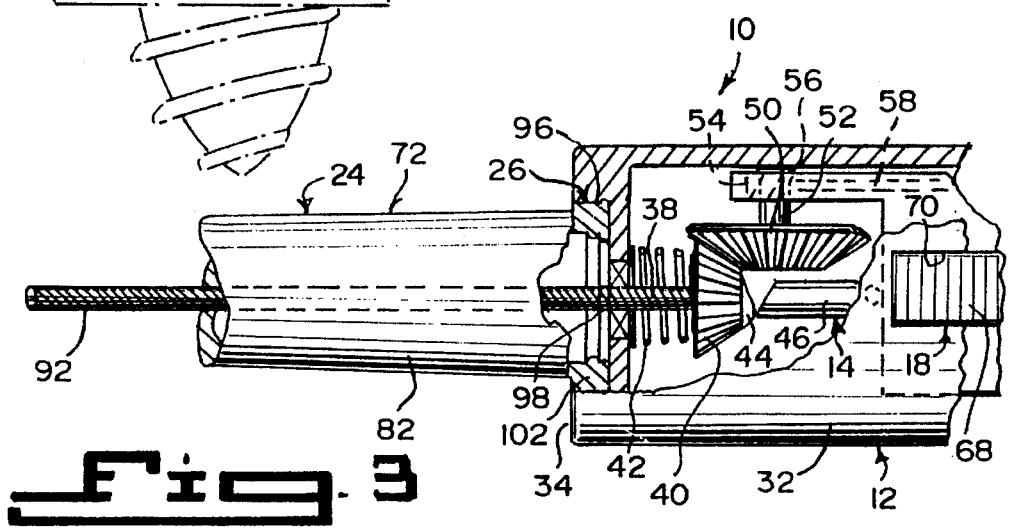
FIG. 3 is a top plan view thereof.

FIG. 3 is an enlarged side view taken in the direction of arrow 3 in FIG. 1, with parts broken away and in section.

FIG. 4 is a side view of the housing with parts broken away and in section, showing the internal drive mechanism therein.

FIG. 5 is a perspective view of the instant invention in the rotating mode to operate the head driver assembly.

FIG. 6 is a perspective view of the instant invention in the oscillating mode to operate the saw assembly.

FIG. 7 is an end view of the rotary switch taken in the direction of arrow 7 in FIG. 6.

Similar reference characters denote corresponding features consistently throughout the attached drawings.

DETAILED DESCRIPTION OF THE PREFERRED EMBODIMENTS

Turning now descriptively to the drawings, in which similar reference characters denote similar elements throughout the several views, FIGS. 1 through 6 illustrate a dental driving device 10 comprising a housing 12 with a driven mechanism 14 within the housing 12. A facility 16 within the housing 12 is for driving the driven mechanism 14. A component 18 within the housing 12 is for selectively placing the driven mechanism 14 in a rotating mode 20 and in an oscillating mode 22. A rotatable tool implement 24 is provided, as shown in FIGS. 1 through 5. An element is for coupling the rotatable tool implement 24 to the housing 12 in a removable manner. When the selectively placing component 18 is put in the rotating mode 20, the driving facility 16 will operate the driven mechanism 14 and cause the rotatable tool implement 24 to turn about an axis. An oscillating tool implement 28 is also provided, as shown in FIG. 6. Another element 30 is for coupling the oscillating tool implement 28 to the housing 12 in a removable manner. When the selectively placing component 18 is put in the oscillating mode 22, the driving facility 16 will operate the driven mechanism 14 and cause the oscillating tool implement 28 to swing back and forth.

The housing 12 is a hollow cylindrical body 32, having a first end wall 34 and a second end wall 36. The hollow cylindrical body 32 can be grasped in a hand of a person using the device 10.

The driven mechanism 14 includes a first stub shaft 38 carried in the first end wall 34 of the hollow cylindrical body 32. The first stub shaft 38 can rotate and oscillate in the first end wall 34. A first bevel gear 40 is connected to an inner end of the first stub shaft 38. A spring 42 is on the first stub shaft 38 between the first end wall 34 of the hollow cylindrical body 32 and the first bevel gear 40, so as to bias the first bevel gear 40 away from the first end wall 34. A cam follower 44 is on the first bevel gear 40, opposite from the first stub shaft 38. A cam shaft 46 is mounted in a rotatable manner within the hollow cylindrical body 32, so that it can engage with the cam follower 44. A second bevel gear 48 is affixed to the cam shaft 46 and faces the first bevel gear 40. A third bevel gear 50 is mounted in a slideable manner between the first bevel gear 40 and the second bevel gear 48. A second stub shaft 52 is affixed to the third bevel gear 50. a worm gear 54 is attached to the second stub shaft 52. A worm 56 is in engagement with the worm gear 54. An elongated shaft 58 is connected at a first end to the worm 56 and extends rearwardly towards the second end wall 36 of the hollow cylindrical body 22.

The driving facility 16 consists of a motor 60 mounted within the hollow cylindrical body 32 adjacent the second end wall 36. A drive shaft 62 extends inwardly from the motor 60. A spur gear 64 is affixed to the drive shaft 62. A spur pinion 66 is affixed to a second end of the elongated shaft 58, whereby the spur pinion 66 is in engagement with the spur gear 64.

The selectively placing component 18 is a shuttle valve 68 located in a longitudinal slot 70 in the hollow cylindrical body 32 and coupled to the elongated shaft 58, to allow the elongated shaft 58 to rotate. When the shuttle valve 68 is moved into a forward position in the longitudinal slot 70, the third bevel gear 50 will contact the first bevel gear 40 in the rotating mode 20. When the shuttle valve 68 is moved into a rear position in the longitudinal slot 70, the third bevel gear 50 will contact the second bevel gear 48 in the oscillating mode 22.

The rotatable tool implement 24 is a head driver assembly 72 for inserting a pin implant 74 into a bone 76 below a gum 78 in a mouth, for attachment of a crown 80. The head driver assembly includes an elongated neck 82. A stationary head portion 84 is connected to a first end of the elongated neck 82. A rotary head portion 86 has roller bearings 88 connected to the stationary head portion 84. A gripper cup 90 is within the rotary head portion 86 to make contact with the pin implant 74. A flexible shaft 92 extends through the elongated neck 82 and is bent downwards into the stationary head portion 84. A pair of prongs 94 on a first end of the flexible shaft 92 engages with the rotary head portion 86.

The hollow cylindrical body 32 further consists of the first end wall 34 having a socket 96 therein. A connector 98 is on an outer end of the first stub shaft 38. A setscrew 100 adjacent the first end wall 34 extends into the socket 96.

The first coupling element 26 is a clamp member 102 on a second end of the elongated neck 82 of the head driver assembly 72, which snaps into the socket 96. A second end of the flexible shaft 92 can engage with the connector 98. The setscrew 100 can hold the clamp member 102 stationary within the socket 96.

The oscillating tool implement 28, shown in FIG. 6, is a saw assembly 104 for cutting into a tooth 106 in the mouth and in dental models. the saw assembly 104 includes an elongated neck 106. a flexible shaft 108 extends through the elongated neck 106. a U-shaped frame 110 is connected to a first end of the flexible shaft 108. A saw blade 112 is mounted in the U-shaped frame 110.

The second coupling element 30 is a clamp member 114 on a second end of the elongated neck 106 of the saw assembly 104, which snaps into the socket 96. A second end of the flexible shaft 108 can engage with the connector 98. the set screw 100 can hold the clamp member 114 stationary within the socket 96.

A three position rotary switch 116, best seen in FIG. 7, is connected to the motor 60 at the second end 36 of the hollow cylindrical body 32. The first position 118 turns the motor 60 off. The second position 120 turns the motor 60 on. The third position 122 reverses the motor 60.

LIST OF REFERENCE NUMBERS 10 dental tool driving device
12 housing
14 driven mechanism
16 driving facility
18 selectively placing component
20 rotating mode
22 oscillating mode
24 rotatable tool implement
26 first coupling element for 24
28 oscillating tool implement
30 second coupling element for 28
32 hollow cylindrical body for 12
34 first end wall of 32
36 second end wall of 32
38 first stub shaft
40 first bevel gear on 38
42 spring on 38
44 cam follower on 40
46 cam shaft
48 second bevel gear on 46
50 third bevel gear on 52
52 second stub shaft
54 worm gear on 52
56 worm on 58
58 elongated shaft
60 motor
62 drive shaft of 60
64 spur gear on 62
66 spur pinion on 58
68 shuttle valve for 18
70 longitudinal slot in 32
72 head driver assembly for 24
74 pin implant
76 bone
78 gum
80 crown
82 elongated neck of 72
84 stationary head portion
86 rotary head portion
88 roller bearing
90 gripper cup in 86
92 flexible shaft in 82 to 84
94 prong on 92
96 socket in 34
98 connector on 38
100 setscrew
102 clamp member for 26 on 82
104 saw assembly for 28
106 elongated neck of 104
108 flexible shaft in 106
110 U-shaped frame on 108
112 saw blade in 110
114 clamp member for 28 on 106
116 three position switch for 60
118 first position of 114 "off" for 60
120 second position of 114 "on" for 60
122 third position of 114 reverses 60

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A dental tool driving device comprising:
   a) a housing, said housing being a hollow cylindrical body having a first end wall and a second end wall, whereby said hollow cylindrical body can be grasped in a hand of a person using said device;
   b) a driven mechanism within said housing, said driven mechanism including a first stub shaft carried in said first end wall of said hollow cylindrical body, so that said first stub shaft can rotate and oscillate in said first end wall, a first bevel gear connected to an inner end of said first stub shaft, a spring on said first stub shaft between said first end wall of said hollow cylindrical body and said first bevel gear, so as to bias said first bevel gear away from said first end wall, a cam follower on said first bevel gear opposite from said first stub shaft, a cam shaft mounted in a rotatable manner within said hollow cylindrical body, so that it can engage with said cam follower, a second bevel gear affixed to said cam shaft and facing said first bevel gear, a third bevel gear mounted in a slideable manner between said first bevel gear and said second bevel gear, a second stub shaft affixed to said third bevel gear, a worm gear attached to said second stub shaft, a worm in engagement with said worm gear, and an elongated shaft connected at a first end to said worm and extending rearwardly towards said second end wall of said hollow cylindrical body;
   c) means within said housing for driving said driven mechanism;
   d) means within said housing for selectively placing said driven mechanism in a rotating mode and in an oscillating mode;
   e) a rotatable tool implement;
   f) means for coupling said rotatable tool implement to said housing in a removable manner, so that when said selectively placing means is put in the rotating mode, said diving means will operate said driven mechanism and cause said rotatable tool implement to turn about an axis;
   g) an oscillating tool implement; and
   h) means for coupling said oscillating tool implement to said housing in a removable manner, so that when said selectively placing means is put in the oscillating mode, said driving means will operate said driven mechanism and cause said oscillating tool implement to swing back and forth.

2. A dental tool driving device as recited in claim 3, wherein said driving means includes:
   a) a motor mounted within said hollow cylindrical body adjacent said second end wall;
   b) a drive shaft extending inwardly from said motor;
   c) a spur gear affixed to said drive shaft; and
   d) a spur pinion affixed to a second end of said elongated shaft, whereby said spur pinion is in engagement with said spur gear.

3. A dental tool driving device as recited in claim 2, wherein said selectively placing means is a shuttle valve located in a longitudinal slot in said hollow cylindrical body coupled to said elongated shaft to allow said elongated shaft to rotate, when said shuttle valve in the longitudinal slot is moved into a forward position, said third bevel gear will contact said first bevel gear in the rotating mode, and when said shuttle valve in the longitudinal slot is moved into a rear position, said third bevel gear will contact said second bevel gear in the oscillating mode.

4. A dental tool driving device as recited in claim 3, wherein said rotatable tool implement is a head driver assembly for inserting a pin implant into a bone below a gum in a mouth, for attachment of a crown, said head driver assembly includes:
   a) an elongated neck;
   b) a stationary head portion connected to a first end of said elongated neck;
   c) a rotary head portion having roller bearings connected to said stationary head portion;
   d) a gripper cup within said rotary head portion to make contact with the pin implant;
   e) a flexible shaft extending through said elongated neck and bent downwards into said stationary head portion; and
   f) a pair of prongs on a first end of said flexible shaft engaging with said rotary head portion.

5. A dental tool driving device as recited in claim 4, wherein said hollow cylindrical body further includes:
   a) said first end wall having a socket therein;
   b) a connector on an outer end of said first stub shaft; and
   c) a setscrew adjacent said first end wall extending into said socket.

6. A dental tool driving device as recited in claim 5, wherein said first coupling means is a clamp member on a second end of said elongated neck of said head driver assembly which snaps into said socket, so that a second end of said flexible shaft can engage with said connector and said setscrew can hold said clamp member stationary within said socket.

7. A dental tool driving device as recited in claim 6, wherein said oscillating tool implement is a saw assembly for cutting into a tooth in the mouth and in dental models, said saw assembly includes:
   a) an elongated neck;
   b) a flexible shaft extending through said elongated neck;
   c) a U-shaped frame connected to a first end of said flexible shaft; and
   d) a saw blade mounted in said U-shaped frame.

8. A dental tool driving device as recited in claim 7, wherein said second coupling means is a clamp member on a second end of said elongated neck of said saw assembly which snaps into said socket, so that a second end of said flexible shaft can engage with said connector and said setscrew can hold said clamp member stationary within said socket.

9. A dental tool driving device as recited in claim 8, further including a three position rotary switch connected to said motor at said second end of said hollow cylindrical body, wherein said first position turns said motor off, said second position turns said motor on and said third position reverses said motor.

* * * * *